US011602327B2

(12) United States Patent
Lafon et al.

(10) Patent No.: US 11,602,327 B2
(45) Date of Patent: Mar. 14, 2023

(54) METHOD AND SYSTEM FOR LOCALIZING A REGION OF INTEREST IN A MEDIUM IN WHICH CAVITATION OCCURS (71) Applicants: INSERM (INSTITUT NATIONAL DE LA SANTE ET DE LA RECHERCHE MEDICALE), Paris (FR); CENTRE LEON BERARD, Lyons (FR); UNIVERSITE CLAUDE BERNARD LYON 1, Villeurbanne (FR); TOHOKU UNIVERSITY, Miyagi (JP)

(72) Inventors: Cyril Lafon, Lyons (FR); Jean-Louis Mestas, Lyons (FR); Maxime Lafond, Lyons (FR); Shin-Ichiro Umemura, Sendai (JP)

(73) Assignees: INSERM (INSTITUT NATIONAL DE LA SANTE ET DE LA RECHERCHE MEDICALE), Paris (FR); CENTRE LEON BERARD, Lyons (FR); UNIVERSITE CLAUDE BERNARD LYON 1, Villeurbanne (FR); TOHOKU UNIVERSITY, Miyagi (JP)

(*) Notice: Subject to any disclaimer, the term of this patent is extended or adjusted under 35 U.S.C. 154(b) by 529 days.

(21) Appl. No.: 16/326,294

(22) PCT Filed: Aug. 28, 2017

(86) PCT No.: PCT/EP2017/071497
§ 371 (c)(1),
(2) Date: Feb. 18, 2019

(87) PCT Pub. No.: WO2018/037130
PCT Pub. Date: Mar. 1, 2018

(65) Prior Publication Data
US 2019/0175146 A1   Jun. 13, 2019

(30) Foreign Application Priority Data

Aug. 26, 2016  (EP) ..................... 16306088

(51) Int. Cl.
*A61B 8/00* (2006.01)
*A61B 8/08* (2006.01)
(Continued)

(52) U.S. Cl.
CPC ............... *A61B 8/469* (2013.01); *A61B 8/08* (2013.01); *A61B 8/5223* (2013.01); *A61N 7/02* (2013.01);
(Continued)

(58) Field of Classification Search
CPC ......... A61B 8/469; A61B 8/5223; A61B 8/08; A61B 2017/22007; A61B 2017/22008;
(Continued)

(56) References Cited

U.S. PATENT DOCUMENTS 5,827,204 A    10/1998  Grandia et al.
6,406,429 B1    6/2002  Bar-Cohen et al.
(Continued)

FOREIGN PATENT DOCUMENTS

WO    2013/132060 A1    9/2013

OTHER PUBLICATIONS

"Multilateration", Wikipedia, Wikimedia Foundation, modified Aug. 26, 2015, https://web.archive.org/web/20151123072524/https://en.wikipedia.org/wiki/Multilateration#TDOA_geometry (Year: 2015).*
(Continued)

*Primary Examiner* — Shahdeep Mohammed
(74) *Attorney, Agent, or Firm* — WCF IP (57) ABSTRACT

Method and system for localizing a region of interest in a medium in which cavitation occurs. Method for localizing a region of interest (R) in a medium (M) in which cavitation
(Continued)

occurs, the method comprising the steps consisting in: producing cavitation in the region of interest (R), the cavitation generating an acoustic signal, at each of at least three separate positions, detecting a cavitation signal representative of the acoustic signal of the cavitation, for at least two pairs of cavitation signals, determining a delay between the cavitation signals of each pair of cavitation signals, calculating a localization of the region of interest (R) based on the delays and the positions.

8 Claims, 11 Drawing Sheets (51) Int. Cl.
*A61N 7/02* (2006.01)
*A61N 7/00* (2006.01)
*A61B 17/22* (2006.01)

(52) U.S. Cl.
CPC ............... *A61B 2017/22007* (2013.01); *A61N 2007/0039* (2013.01); *A61N 2007/0078* (2013.01); *A61N 2007/027* (2013.01)

(58) Field of Classification Search
CPC .............. A61N 7/02; A61N 2007/0039; A61N 2007/0078; A61N 2007/027; G01N 29/036; G01N 29/221; G01N 29/348; G01N 29/42; G01N 29/4409
See application file for complete search history.

(56) References Cited

U.S. PATENT DOCUMENTS

| 9,238,152 B2 | 1/2016 | Coussios et al. |
| 2015/0141734 A1* | 5/2015 | Chapelon ................. A61N 7/02 600/2 |

OTHER PUBLICATIONS

Sim, Min Seop, et al. "Underwater acoustic source localization using closely spaced hydrophone pairs." Japanese Journal of Applied Physics 55.7S1 (2016): 07KG05. (Year: 2016).*

Lafond, Maxime, et al. "Evaluation of a three-hydrophone method for 2-D cavitation localization." IEEE transactions on ultrasonics, ferroelectrics, and frequency control 65.7 (2018): 1093-1101. (Year: 2018).*

Chan, Yiu-Tong, and K. C. Ho. "A simple and efficient estimator for hyperbolic location." IEEE Transactions on signal processing 42.8 (1994): 1905-1915. (Year: 1994).*

Li, Tong, et al. "Passive cavitation detection during pulsed HIFU exposures of ex vivo tissues and in vivo mouse pancreatic tumors." Ultrasound in medicine & biology 40.7 (2014): 1523-1534. (Year: 2014).*

"Euclidian distance", Wikipedia, Wikimedia Foundation, modified Feb. 21, 2016, https://web.archive.org/web/20160422050734/https://en.wikipedia.org/wiki/Euclidean_distance (Year: 2016).*

* cited by examiner

METHOD AND SYSTEM FOR LOCALIZING A REGION OF INTEREST IN A MEDIUM IN WHICH CAVITATION OCCURS

The invention relates to a method and a system for localizing a region of interest in a medium in which cavitation occurs.

Cavitation designates formation and/or movement of gas and/or vapour bubbles in the medium. These bubbles can dynamically oscillate and/or collapse, thereby producing a very localized shock wave, a punctual increase of temperature or any other mechanical and/or chemical effect. In particular, acoustic cavitation is a stochastic process, initiated with ultrasound (US), which has been widely investigated (Coussios and Roy, 2008; Leighton, 1994). Two types of cavitation can co-exist: stable regime (oscillations of gas bubbles) and inertial regime (violent collapse of the bubbles due to stronger pressures). Bubbles clouds present interesting acoustic features. When gas bubbles encounter an excitation sound wave, both of the cavitation regimes can be characterized by a specific acoustic signature from the scattered wave.

Cavitation can be considered as an undesired side effect for some treatments like thermal ablation of brain tumors with High Intensity Focused Ultrasound. But cavitation finds also particular applications in clinics for cavitation-based treatments which include for examples tissue erosion (histotripsy) or brain-blood-barrier opening for delivery of therapeutic material in the brain and potentiation of chemotherapeutics. In particular, anti-tumor effects obtained by cavitation-related techniques are promising (Mitragotri, 2005; Rosenthal et al., 2004; Umemura et al., 1997).

Whether cavitation is considered as an adverse effect or the therapeutic mechanism, the path toward clinical transfer of such cavitation technique requires proper monitoring, notably of the cavitation phenomenon. In the context of clinical applications, the complete characterization of the cavitation activity includes also the cavitation localization. In this area, various methods use beam forming with conventional ultrasound scanner (Gyongy and Coussios, 2010) or ultrafast echo-imaging (Prieur et al., 2015) to locate the cloud in the uncorrelated area. Also, qualitative evaluation of cavitation presence can be performed by visualizing the hyper-echoic zone created by the bubbles (Lafond et al., 2016).

However, these methods come with limitations. Notably, the broadband frequency of the echo-imager does not allow the localization and characterization of stable cavitation. Since the intensity of cavitation has to be intense, an important post-processing time is required, thereby preventing real-time modalities. Finally, the cost of such equipment is prohibitive for developments of clinical devices.

The invention aims to solve the above mentioned problems

To this end, according to a first aspect, the invention provides a method for localizing a region of interest in a medium in which cavitation occurs, the method comprising the steps consisting in:
 producing cavitation in the region of interest, the cavitation generating an acoustic signal,
 at each of at least three separate positions, detecting a cavitation signal representative of the acoustic signal of the cavitation,
 for at least two pairs of cavitation signals, determining a delay between the cavitation signals of each pair of cavitation signals,
 calculating a localization of the region of interest based on the delays and the positions,
wherein the step of determining the delay comprises, for each pair of cavitation signals:
 incrementally shifting one of the cavitation signal with respect to the other according to a time pitch,
 at each time pitch, comparing the cavitation signals,
 identifying a maximum inter-correlation time pitch as the time pitch at which the cavitation signals overlap at a maximum,
 calculating the delay as a sum of the time pitches up to the maximum inter-correlation time pitch.

Hence, the invention makes use of an extended envelope of the cavitation signals which enables the cavitation to be localized in a simple, fast and reliable manner. In addition to an enhanced efficiency, the method requires only a low number of equipment, which makes it very cost-effective.

Since the method is fully-passive, it can be directly integrated on a clinical system. The calculated position may be indicated as a point which makes easier conditional monitoring to assess the correct reaching of a specific target area. In the context of cavitation-related therapy, it is thus expected to increase the reliability level of cavitation applications, giving it more credit for clinical translation.

According to some provisions, the method may be used as a characterization tool for cavitation characterization to optimize the efficacy of cavitation-based treatments. Also, the method could be easily implemented in a real time control loop.

The step of calculating a localization of the region of interest may comprise:
 converting the delays in distance,
 for a number of points of a space including the region of interest, each point having determined coordinates (x, y), minimizing the cost-function $$C(x, y) = \sum_{i=2}^{n} [(r_1(x, y) - r_i(x, y)) - \varepsilon_i]^2 \quad (1)$$

with n integer greater than or equal to 3 is the number of positions, $$r_i = \left\| \begin{array}{c} x_i - x \\ y_i - y \end{array} \right\|,$$

the distance between the position i and the point (x, y), $\varepsilon_i$, the distance between the positions of receptors i and 1 determined from the conversion of the delays in distance.

Alternatively, the step of calculating a localization of the region of interest may comprise solving hyperbolic solutions defined by the following equation (2):

$$r_i^2 = K_i - 2x_i x - 2y_i y + x^2 + y^2, \; 1=1, \ldots, n \quad (2)$$

with n integer greater than or equal to 3 is the number of positions, $$r_i = \left\| \begin{array}{c} x_i - x \\ y_i - y \end{array} \right\|,$$

the distance between the position numbered i and a point having coordinates (x, y) that are searched and corresponding to a position of the acoustic source (the cavitation cloud), $K_i = x_i^2 + y_i^2$, wherein the solving of hyperbolic solutions comprises:
the delay measured between the positions i and 1 being $r_{i,1} = r_i - r_1$, $r_i^2 = (r_{i,1} + r_1)^2$ and equation (2) corresponds to:

$$r_{i,1}^2 + 2r_{i,1}r_1 + r_1^2 + K_i - 2x_ix - 2y_iy + x^2 + y^2 \quad (3)$$

subtracting equation (2) to equation (3) so that $$r_{i,1}^2 + 2r_{i,1}r_1 = -2x_{i,1}x - 2y_{i,1}y + K_i - K_1 \quad (4)$$

with $x_{i,1} = x_i - x_1$ and $y_{i,1} = y_i - y_1$
solving equation (4) in terms of $r_1$ for n=3 that is:

$$\begin{bmatrix} x \\ y \end{bmatrix} = -\begin{bmatrix} x_{2,1} & y_{2,1} \\ x_{3,1} & y_{3,1} \end{bmatrix}^{-1} \times \left\{ \begin{bmatrix} r_{2,1} \\ r_{3,1} \end{bmatrix} r_1 + \frac{1}{2} \begin{bmatrix} r_{2,1}^2 - K_2 + K_1 \\ r_{3,1}^2 - K_3 + K_1 \end{bmatrix} \right\} \quad (5)$$

inserting equation (5) into equation (2) for i=1 to obtain a quadratic equation in $r_1$,
substituting back the positive root into equation (5) to produce solutions in x and y. The step of detecting the cavitation signal may comprise providing at least three hydrophones at respective separate positions and directing the hydrophones towards an area including the region of interest.

The acoustic signal of the cavitation may have at least one specific frequency. The method may comprise, before the step of determining the delay, a step consisting in filtering each cavitation signal with a bandwidth around the specific frequency, the bandwidth being preferably between 25% and 75% of the specific frequency and more preferably between 30% and 60% of the specific frequency. These provisions enable the processing of the cavitation signals to be reduced to a frequency of interest, especially around a sub-harmonic frequency as it will become apparent from the following. Such focusing on specific characteristics of oscillating bubbles of the cavitation enables an actual detection of an acoustic source of the cavitation rather than a detection of an image of the acoustic mirror formed by the water/gas bubble interfaces. Such filtering of the raw signals around the specific frequency, especially the half sub-harmonic, provides a great improvement in the accuracy of the method. The frequency bandwidth is further adjusted in order to provide a suitable ratio between harmonic signal and broadband noise.

The step of producing cavitation may comprise emitting at least first and second ultrasound beams along first and second directions intersecting at a focal point, the first and second ultrasound beams being adapted to generate cavitation in a focal area around the focal point.

When the step of detecting the cavitation signal implements hydrophones, the step of detecting the cavitation signal may comprise directing the hydrophones towards the focal area.

When the method comprises the step consisting in filtering each cavitation signal, the first and second ultrasound beams may have an emission frequency $f_e$, and the specific frequency of the acoustic signal of the cavitation may be between $0.4 \times f_e$ and $0.6 \times f_e$.

When the method comprises the step consisting in filtering each cavitation signal, the first and second ultrasound beams have an emission frequency $f_e$, and the specific frequency of the acoustic signal of the cavitation is between $1.2 \times f_e$ and $2.2 \times f_e$.

Therefore, according to a second aspect, the invention provides a system for localizing a region of interest in a medium in which cavitation occurs, the system comprising:

a cavitation device configured to produce cavitation in the region of interest, the cavitation generating an acoustic signal,
at least three sensors arranged at respective separate positions and configured to detect a cavitation signal representative of the acoustic signal of the cavitation,
a processing unit configured to:
for at least two pairs of cavitation signals, determine a delay between the cavitation signals of each pair of cavitation signals,
calculate a localization of the region of interest based on the delays and the positions,
wherein to determine the delay, the processing unit may be configured to, for each pair of cavitation signals:
incrementally shift one of the cavitation signal with respect to the other according to a time pitch,
at each time pitch, compare the cavitation signals,
identify a maximum inter-correlation time pitch as the time pitch at which the cavitation signals overlap at a maximum,
calculate the delay as a sum of the time pitches up to the maximum inter-correlation time pitch.

The sensors may be hydrophones directed towards an area including the region of interest. The system is therefore simple in structure as it may use only three hydrophones, using one of them twice for the delay determination.

The acoustic signal of the cavitation may have at least one specific frequency, and the processing unit may be configured to, before determining the delay, filter each cavitation signal with a bandwidth around the specific frequency, the bandwidth being preferably between 25% and 75% of the specific frequency and more preferably between 30% and 60% of the specific frequency.

The cavitation device may comprise at least first and second ultrasound transducers configured to emit first and second ultrasound beams along first and second directions intersecting at a focal point, the first and second ultrasound beams being adapted to generate cavitation in a focal area around the focal point.

When the sensors are hydrophones, the hydrophones may be directed towards the focal area.

At least two hydrophones may be mounted respectively onto the first and second ultrasound transducers. In this way, the amount of energy of the useful acoustic signal can be maximized.

When the processing unit is configured to filter each cavitation signal, the first and second ultrasound transducers may be controlled to emit the first and second ultrasound beams having an emission frequency $f_e$, and the specific frequency of the acoustic signal of the cavitation may be between $0.4 \times f_e$ and $0.6 \times f_e$.

When the processing unit is configured to filter each cavitation signal, the first and second ultrasound transducers are controlled to emit the first and second ultrasound beams having an emission frequency $f_e$, and the specific frequency of the acoustic signal of the cavitation is between $1.2 \times f_e$ and $2.2 \times f_e$.

Other objects and advantages of the invention will emerge from the following disclosure of a particular embodiment of the invention given as non limitative example, the disclosure being made in reference to the enclosed drawings in which.

Figure 1:
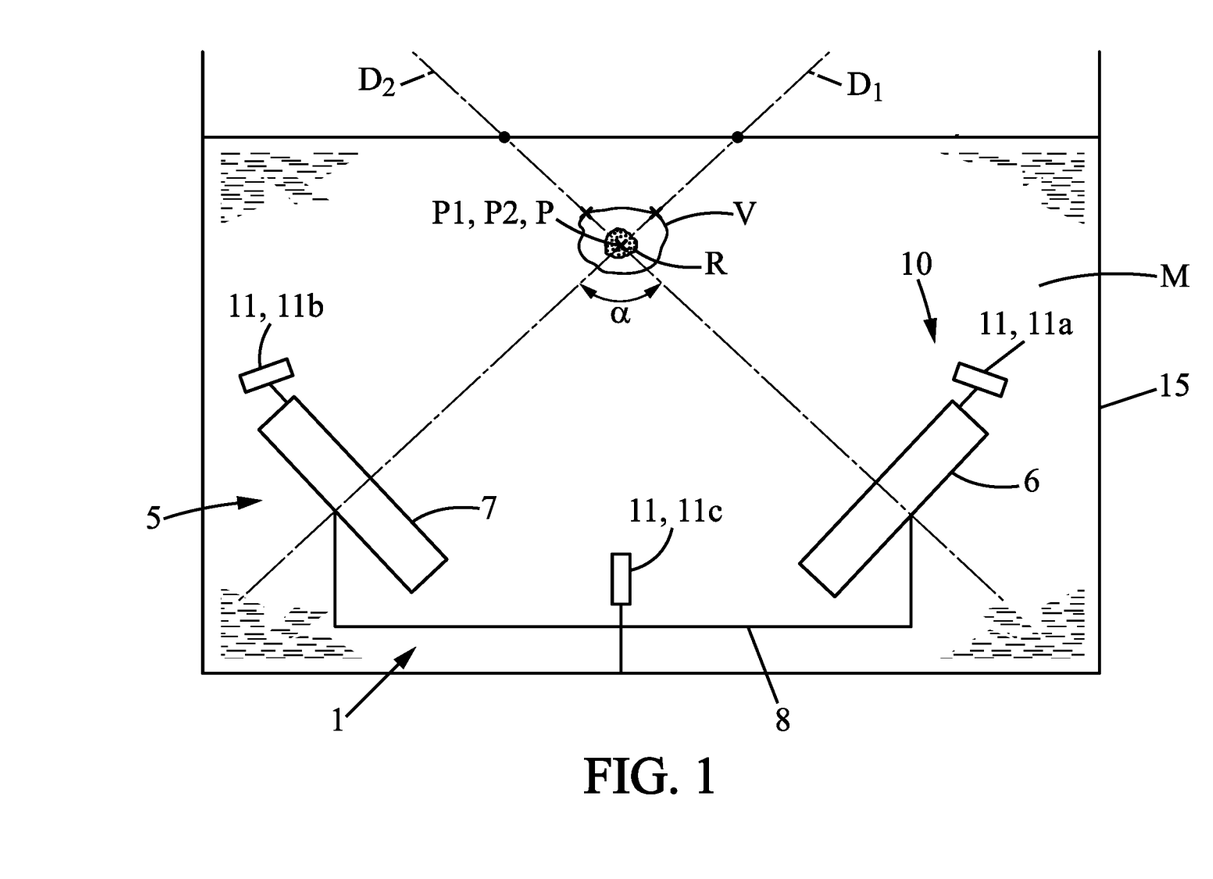
FIG. 1 is a schematic view of a system for localizing a region of interest in a medium in which cavitation occurs according to an embodiment of the invention, the system comprising a cavitation device configured to produce cavitation in the region of interest, three hydrophones arranged at respective separate positions and configured to detect a cavitation signal representative of an acoustic signal of the cavitation.
Figure 2:
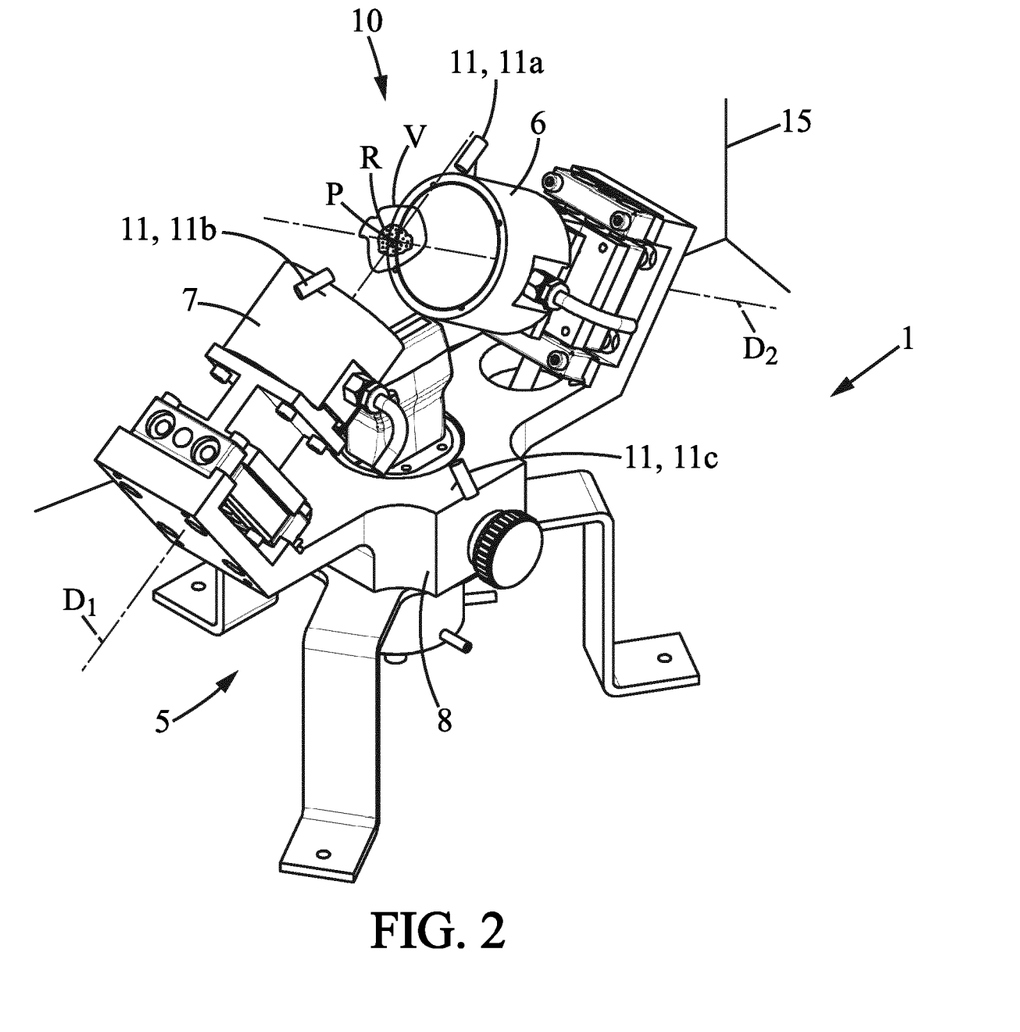
FIG. 2 is a perspective view of the system of FIG. 1.

On the Figures, the same reference numbers refer to the same or similar elements. FIGS. 1 and 2 represent a system 1 for localizing a region of interest R in a medium M in which cavitation occurs. The system 1 is used to implement a method for localizing the region of interest R, which method specifically applies to ultrasonic cavitation-based therapies.

The system 1 comprises a cavitation device 5 configured to produce cavitation in the region of interest R. In the illustrated embodiment, although not limited thereto, the cavitation device 5 implements confocal ultrasound technology of the type disclosed in document WO 2013/132060.

The cavitation device 5 comprises:
a first ultrasound transducer 6 configured to emit a first ultrasound beam along a first direction D1 and focused on a first acoustic focal point P1, and
a second ultrasound transducer 7 configured to emit a second ultrasound beam along a second direction D2 and focused on a second acoustic focal point P2.

The first 6 and second 7 ultrasound transducers may be transducers each adapted to generate an ultrasound beam with an emission frequency comprised between 100 kHz and 10 MHz and preferably between 0.5 MHz and 2 MHz. In a non-limitative example described in details in the following of the description, the first 6 and second 7 ultrasound transducers are focused transducers of 50 mm in diameter and 50 mm in curvature radius.

The first 6 and second 7 ultrasound transducers are mounted on a frame 8 through a moving arrangement enabling each of the first 6 and second 7 ultrasound transducers to be moved with respect to the frame 8 and the other ultrasound transducer 6, 7.

The cavitation device 5 further comprises a control unit connected to the first 6 and second 7 ultrasound transducers and the moving arrangement. In particular, the control unit may control the moving arrangement, possibly driven by a user through a suitable communication interface, so that the first D1 and second D2 directions intersect with an angle α comprised between 30° and 150°, especially between 60° and 120°, for example of 90°, at a focal point P where the first P1 and second P2 acoustic focal point superimpose. The control unit may also control the first 6 and second 7 ultrasound transducers so that the first and second ultrasound beams generate cavitation in a focal area V around the focal point P and including the region of interest R. In particular, the first 6 and second 7 ultrasound beams may be emitted between 1 MHz and 1.2 MHz as emission frequency. In the non-limitative example, the emission frequency is 1.1 MHz.

The invention is disclosed in relation with a cavitation device 5 implementing confocal ultrasound technology based on two intersecting ultrasound beams to generate cavitation. In other embodiments, the cavitation device 5 could, however, have more than one first ultrasound transducer 6 and/or more than one second ultrasound transducer 7 to implement confocal ultrasound technology. Ultrasound technology could also be used differently to produce cavitation in the focal area V, for example implementing only one ultrasound transducer. For example, one or more ultrasound beams could be used to activate a poration medium containing microbubbles. Furthermore, the invention is not limited to ultrasound technology and may implement any other kind of technology to produce cavitation in the region of interest R.

The system 1 also comprises a localization device 10 specifically designed for localizing the region of interest R in which cavitation generated by the cavitation device 5 occurs. Localization of the cavitation is based on detection of an acoustic signal generated by the cavitation. The acoustic signal is indicative of a nature and an intensity of the cavitation activity and is characterized by one or several specific frequencies among which sub-harmonics of the emission frequency $f_e$, and especially a half sub-harmonic, namely a frequency between 0.4 and 0.6 times the emission frequency $f_e$ of the first 6 and second 7 ultrasound transducers. In particular, the specific frequency of the half sub-harmonic may be between 500 kHz and 600 kHz. In the non-limitative example, the specific frequency of the half sub-harmonic is 550 kHz. Other specific frequency of the acoustic signal could be used such as ultra-harmonics of the emission frequency $f_e$, and especially an ultra-harmonic between 1.2 and 2.2 times the emission frequency $f_e$, for example of 1.5 times the emission frequency $f_e$ or twice the emission frequency $f_e$.

The localization device 10 comprises three hydrophones 11 as sensors configured to detect a cavitation signal C representative of the acoustic signal of the cavitation. The hydrophones 11 are arranged at respective separate positions to be able to provide localization information including at least two pairs of cavitation signals C. To maximize an amount of acoustic signal received by each hydrophone 11 and thereby the reliability of the localization, the hydrophones 11 are directed towards an area including the region of interest R, namely the focal area V in the illustrated embodiment. In particular, first 11a and second 11b hydrophones are mounted respectively onto the first 6 and second 7 ultrasound transducers. A third hydrophone 11c is mounted on the frame 8 between the first 11a and second 11b hydrophones.

In other embodiments, the localization device 10 could comprise any other arrangement of three or more sensors each configured to detect a cavitation signal C representative of the acoustic signal of the cavitation and to provide two or more pairs of cavitation signals. In particular, in another embodiment shown on FIG. 11, the hydrophones 11 are mounted on a movable arm 20.

To enable localization of the cavitation, the localization device 10 further has a processing unit, possibly connected to the control unit of the cavitation device 5; for processing the cavitation signals.

Figure 3:
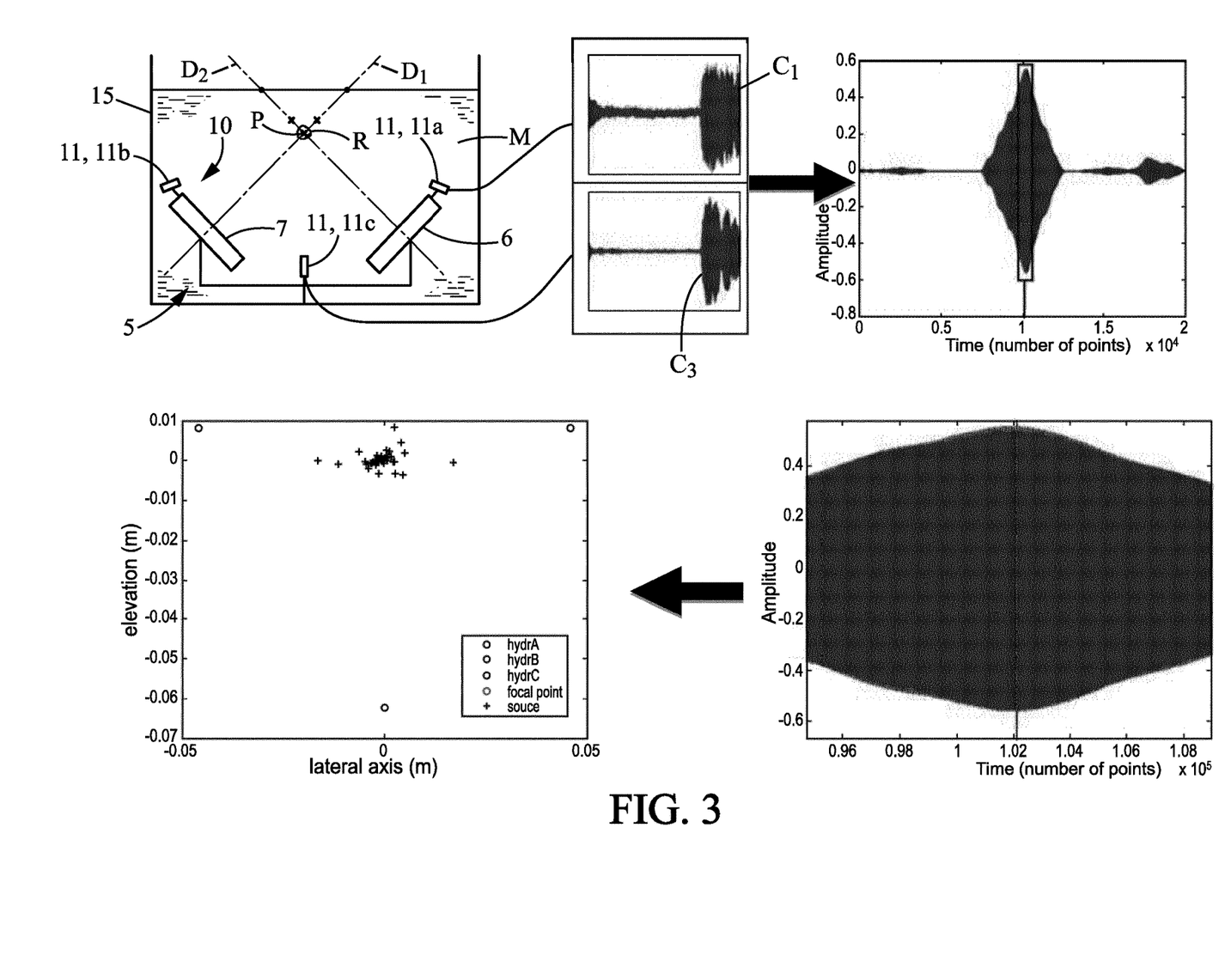
FIG. 3 illustrates a method for localizing a region of interest in a medium in which cavitation, the method implementing the system of FIG. 1 and comprising calculating a localization of the region of interest based on delays between the cavitation signals of pairs of cavitation signals and the positions of the hydrophones, FIG. 4 provides a comparison between the region of interest localized on a picture acquired by a camera and the region of interest localized by the method in eight cavitation experiments, the method being implemented with or without filtering cavitation signals.

A processing of the cavitation signals is now disclosed in relation to FIG. 3.

To enhance accuracy of the localization by taking sufficient information from the acoustic signal while removing noise, the processing unit may filter each cavitation signal C with a bandwidth around the specific frequency of the acoustic signal of the cavitation. The specific frequency of the acoustic signal of the cavitation may be chosen between sub-harmonics of the emission frequency $f_e$, especially around the half sub-harmonic of 550 kHz. The bandwidth can be between 25% and 75% of the specific frequency and preferably between 30% and 60% of the specific frequency. In the case of the half sub-harmonic of 550 kHz, the bandwidth may be between 100 kHz and 300 kHz, especially about 200 kHz. Alternatively, the specific frequency of the acoustic signal of the cavitation may be chosen between ultra-harmonics of the emission frequency $f_e$7. Method according to any of claims 4 and 5 when dependent on claim 3, wherein the first and second ultrasound beams have an emission frequency $f_e$, and wherein the specific frequency of the acoustic signal of the cavitation is between $1.4 \times f_e$ and $1.6 \times f_e$.

For two pairs of cavitation signals C, namely a first pair comprising the cavitation signals C1, C3 of the first 11a and third 11c hydrophones and a second pair comprising the cavitation signals C2, C3 of the second 11b and third 11c hydrophones, the processing unit determines a delay between the cavitation signals of each pair of cavitation signals.

The delay is determined by inter-correlation maxima detection. In particular, for the first pair of cavitation signals C1, C3, the processing unit is configured to incrementally shift the cavitation signal of the first hydrophone 11a with respect to the third hydrophone 11c according to a time pitch. At each time pitch, the processing unit compares the cavitation signals C1, C3 of the first 11a and third 11c hydrophones. The time pitch at which the cavitation signals C1, C3 of the first 11a and third 11c hydrophones overlap at a maximum, namely an integral of the difference is minimized, is then identified as a maximum inter-correlation time pitch. The processing unit may then sum the time pitches up to the maximum inter-correlation time pitch to obtain the delay.

The step of determining the delay between the cavitation signals of each pair of cavitation signals can be performed on an extended envelope of each cavitation signal, either in the selected bandwidth, as disclosed previously in relation with FIG. 3 or on the whole cavitation signal. Alternatively, this step of determining the delay between the cavitation signals of each pair of cavitation signals can be performed on a global shape, of each cavitation signal. Cavitation signals can then be appropriately pre-processed, possibly in the selected bandwidth, to define their respective shapes.

The same inter-correlation maxima detection is performed for the second pair of cavitation signals C2, C3 to obtain enough localization information enabling localization of the region of interest R.

A step of calculating a localization of the region of interest R can be performed by any one of two calculation methods.

A calculation method comprises:
converting the delays in distance,
for a number of point of a space including the region of interest, each point having determined coordinates (x, y), minimizing the cost-function $$C(x, y) = \sum_{i=2}^{n} [(r_1(x, y) - r_i(x, y)) - \varepsilon_i]^2 \quad (1)$$

with n integer greater than or equal to 3 is the number of positions, $$r_i = \left\| \begin{matrix} x_i - x \\ y_i - y \end{matrix} \right\|,$$

the distance between the position of the sensor numbered i and the point (x, y), $\varepsilon_i$, the distance between the positions of sensors i and 1 determined from the conversion of the delays in distance.

Alternatively, another calculation method comprises solving hyperbolic solutions. Such method is disclosed in Y. T. Chan and K. C. Ho, "A simple and efficient estimator for hyperbolic location," *IEEE Trans. Signal Process.*, vol. 42, no. 8, pp. 1905-1915, August 1994.

In the case of an arbitrary distribution in space of three sensors, the following equation (2) can be directly written:

$$r_i^2 = K_i - 2x_i x - 2y_i y + x^2 + y^2, \, 1 = 1, \ldots, n \quad (2)$$

with n integer greater than or equal to 3 is the number of positions, $$r_i = \left\| \begin{matrix} x_i - x \\ y_i - y \end{matrix} \right\|,$$

the distance between the position of the sensor numbered i and a point having coordinates (x, y) that are searched and corresponding to a position of the acoustic source (the cavitation cloud), $$K_i = x_i^2 + y_i^2$$

Since the delay measured between the positions i and 1 is $r_{i,1} = r_i - r_1$, then $r_i^2 = (r_{i,1} + r_1)^2$ and equation (2) corresponds to:

$$r_{i,1}^2 + 2r_{i,1}r_1 + r_1^2 + K_i - 2x_i x - 2y_i y + x^2 + y^2 \quad (3)$$

Subtracting equation (2) to equation (3) results in the following equation (4):

$$r_{i,1}^2 + 2r_{i,1}r_1 = -2x_{i,1}x - 2y_{i,1}y + K_i - K_1 \quad (4)$$

with $x_{i,1} = x_i - x_1$ and $y_{i,1} = y_i - y_1$

Equation (4) can be solved in terms of $r_1$ for n=3 that is:

$$\begin{bmatrix} x \\ y \end{bmatrix} = -\begin{bmatrix} x_{2,1} & y_{2,1} \\ x_{3,1} & y_{3,1} \end{bmatrix}^{-1} \times \left\{ \begin{bmatrix} r_{2,1} \\ r_{3,1} \end{bmatrix} r_1 + \frac{1}{2} \begin{bmatrix} r_{2,1}^2 - K_2 + K_1 \\ r_{3,1}^2 - K_3 + K_1 \end{bmatrix} \right\} \quad (5)$$

Inserting equation (5) into equation (2) for i=1 permits to obtain a quadratic equation in $r_1$. The positive root can then be substituted back into equation (4) to produce the solutions in x and y. The solution ambiguity in the quadratic equations can be solved by restricting the region of interest.

EXAMPLE 1

The system 1 and the method for localizing a region of interest R in a medium M in which cavitation occurs are implemented with the above described cavitation 5 and localization 10 devices in a non-limitative example of experimentation.

An estimation of the reliability of the cavitation localization is performed toward high-speed camera observations.

Material and Methods

Cavitation Device 5

Two focused transducers 6, 7 of 50 mm in diameter and 50 mm in curvature radius and operating at 1.1 MHz are mounted in a manner to match their respective acoustic focal point P1, P2 with a 90° angle α. An impedance of the transducers 6, 7 couple is adjusted to 50 ohms to match an amplifier output. The system 1 is placed in a tank 15 filled with partially-degassed water (4 mg/L) as medium M. A single 2750-cycle pulse is generated by a digital waveform generator at a 1.4 Vrms voltage. The signal is then amplified with a 1 kW RF power amplifier 1140LA (E&I, Rochester, N.Y). The negative pressure at the focal point P is estimated to be 13 MPa. At the time of ultrasound emission, a trigger signal is sent to both a recording oscilloscope and the high-speed camera. As previously disclosed, three in-house built PVDF hydrophones 11 are mounted on the cavitation device 5, oriented toward the focal zone V (FIGS. 1 and 2). Cavitation signals C detected by the hydrophones 11 are recorded at the trigger signal using the recording oscilloscope at a sampling frequency of 100 MHz. In the meantime, the cavitation activity is observed with the high-speed camera as described below.

High-Speed Camera Observations

The high-speed camera is placed perpendicularly to the plane of the three hydrophones 11. A red laser is facing the camera, the laser beam passing through the focal area V which can be found using a needle hydrophone. Then, the focus of the camera is adjusted to observe clearly the edge of the hydrophones 11. An area of 1 cm×1.2 cm is observed. Speed recording is set to 32 kfps and 102 images are recorded. A delay of 33 µs with the trigger signal is applied in order to observe the focal area V from the time when the acoustic beams emitted by the ultrasound transducers 6, 7 reached the focal point, where the cavitation is expected to occur. The 3.2 ms recorded period of time (102 images/32 kfps) permit to observe the 2.5 ms of presence of the acoustic signal in the focal area V (2750 cycles/1.1 MHz). In the meantime, cavitation signals C detected by the hydrophones 11 are recorded as described above. From the processed images, the position of a cloud as the region of interest R is estimated in a blind manner (without knowing the position of the source localized by the hydrophones) by three independent operators.

Acoustical Localization of the Cavitation Cloud

The previously disclosed method is a triangulation of the location of the cavitation cloud R based on the delays obtained on three hydrophones 11 with known positions. The cavitation signals C are imported into Matlab software (MathWorks, Natick, Mass.). The delays between the cavitation signals C of the hydrophones 11 are calculated by finding the delay maximizing the inter-correlation between the recorded cavitation signals C as explained previously. The calculated localization of the cloud R is finally superimposed to the images from the camera. The positions calculated here are compared to the positions of the clouds R visually estimated. The mean error is calculated. These operations are repeated after keeping only the broadband of 200 kHz around the sub-harmonic frequency (550 kHz).

Results

Figure 4:
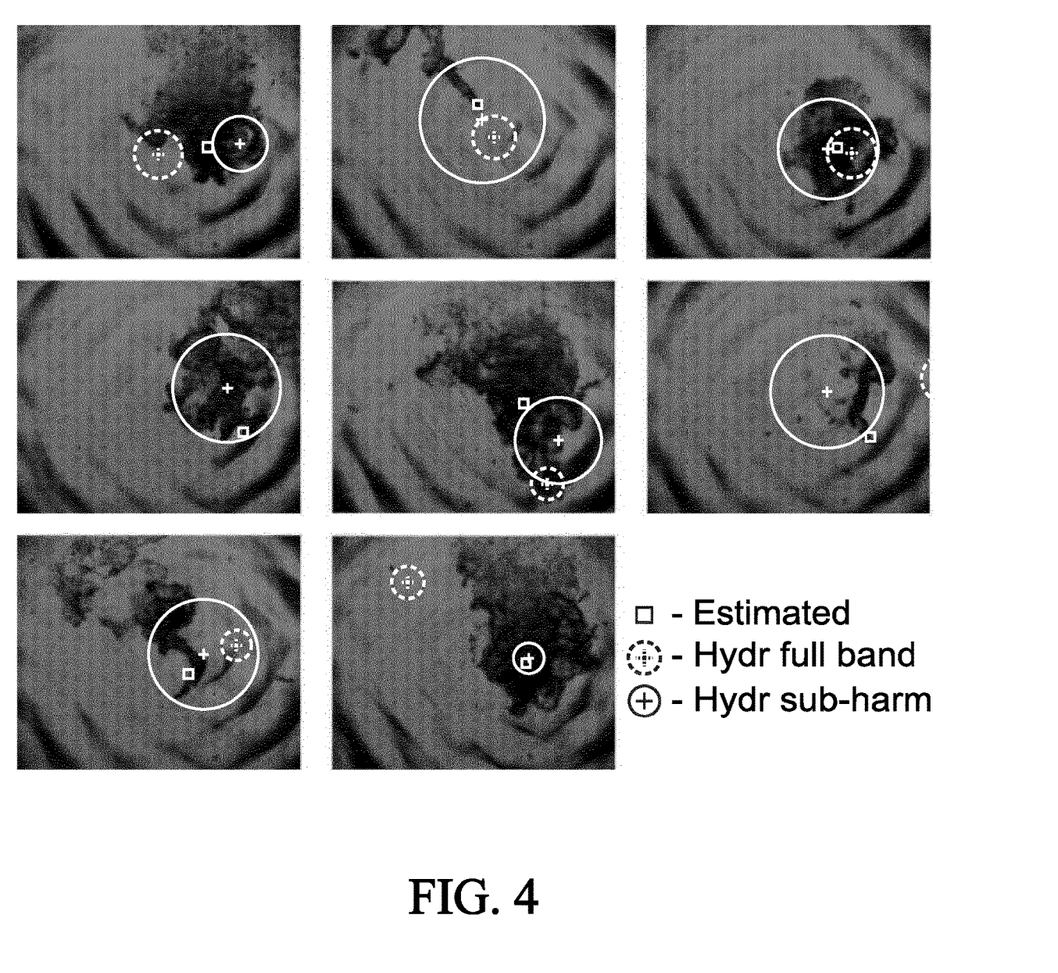

FIG. 4 presents the 60$^{th}$ images of the eight independent cavitation events with the superimposed positions calculated with the localization technique. On FIG. 4, a square circle represents the estimated position of the focal point, the dashed line circle and the full line circle are the localization of the cavitation cloud determined by the method respectively for the full and reduced frequency bandwidth.

The position of the cavitation cloud is calculated with a discrepancy of 3.1±1.8 mm in the case of the full frequency bandwidth. By processing the data only in the 200 kHz frequency band around the 550 kHz sub-harmonic, the accuracy is improved to 1.4±0.8 mm. The circles represent the spatial distance corresponding to the spreading of the intercorrelations (⅔ of the maximum value). The size does not correlate with the intensity of the cavitation activity.

Figure 5:
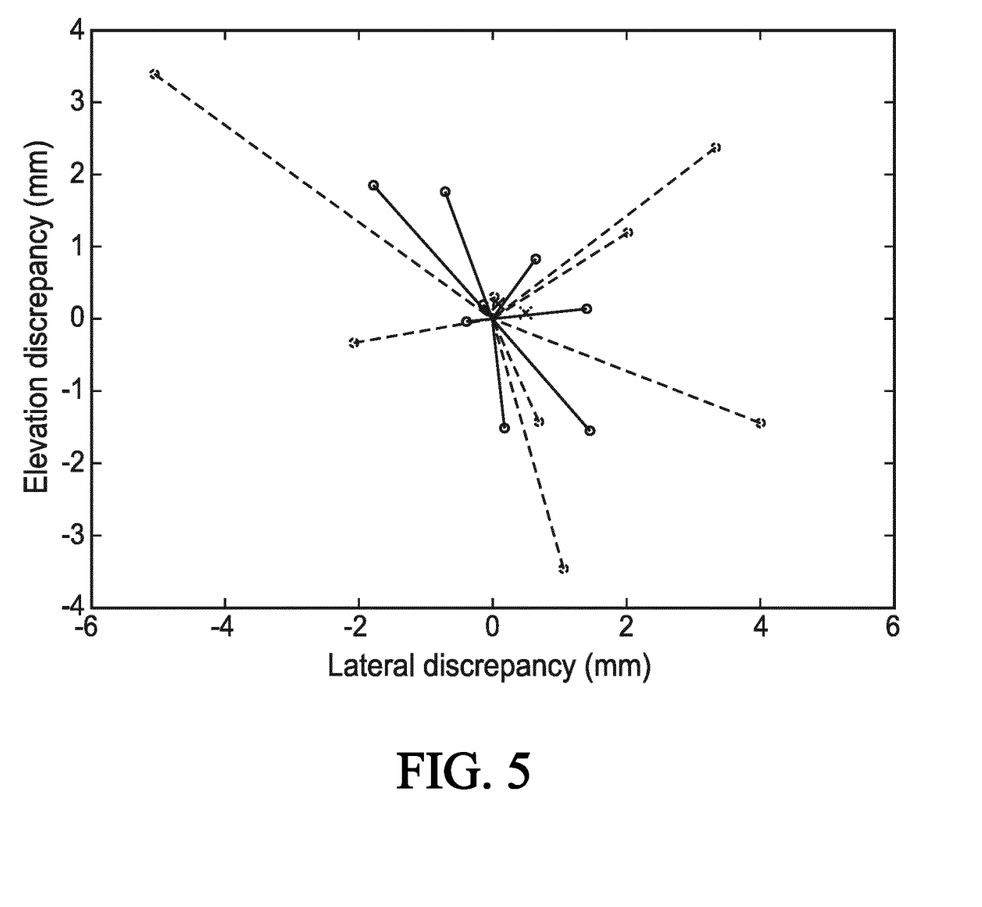
FIG. 5 is a representation of localization discrepancies.

FIG. 5 presents the discrepancies observed as well as the mean discrepancy. Circles and crosses denote for individual and overall mean value, respectively. As previously, dashed line is for full bandwidth and full line is for the filtered cavitation signals. The mean discrepancy indicates that there is no systematic error on the calculated cavitation localization.

Localizations performed with the method based on delays between hydrophones 11 showed a good accuracy. By calculating the inter-correlations using the full frequency bandwidth or only a 200 kHz band around the 550 kHz sub-harmonic, the accuracy of the measured position was 3.1±1.8 mm and 1.4±0.8 mm, respectively. The use of the narrowed bandwidth provides a substantial improvement to the proposed method. Also, it can be seen on the images that the calculated position is always inside or very close to the cavitation cloud.

EXAMPLE 2

Another non-limitative example of experimentation is performed implementing the method of localization of the invention.

Simulation

Figure 6:
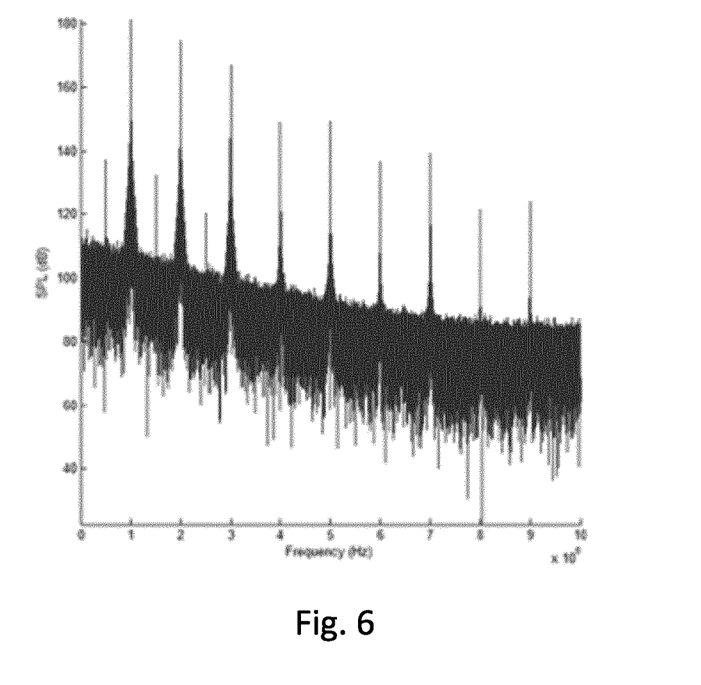
FIG. 6 is a representation of a synthetic cavitation signal emitted by acoustic sources in a simulation of an experimentation involving the method according to the invention.
Figure 7:
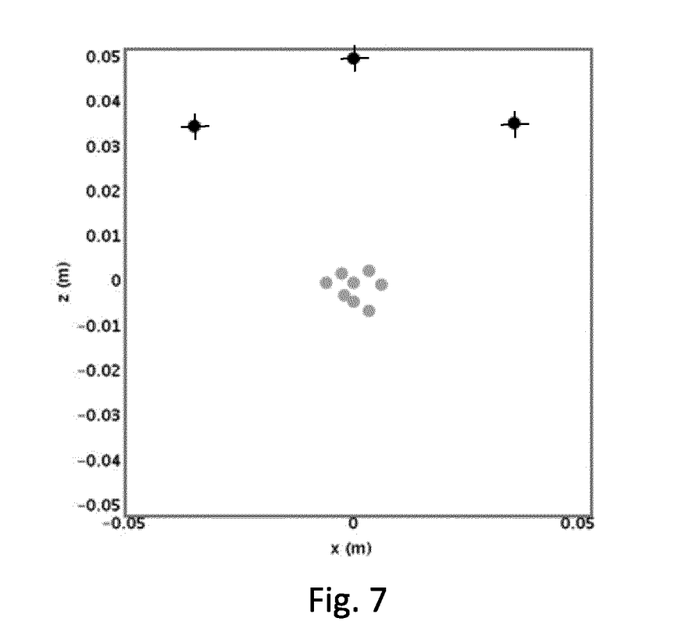
FIG. 7 is a representation of a configuration implemented in the simulation, in which hydrophones are represented by crosses and acoustic sources are represented by dots.

In this numerical experimentation, three sensors and an arbitrary number of acoustic sources are placed in chosen locations in a volume. The acoustic sources are placed in a random manner in an area defined by a spreading of the cavitation cloud as measured in a suitable camera. A synthetic cavitation signal of each acoustic source is created by adding harmonics (decreasing by 3 dB per octave), subharmonic and ultra-harmonics at 40 dB under the corresponding harmonics. Each one of these peaks is then randomly adjusted for each acoustic source within a 6 dB range. A random white-noise of −30 dB is finally added to simulate inertial cavitation. The cavitation signal of each of the acoustic sources is then propagated to each of the sensors. At this point, another random noise is included to state for the measurement noise. The FIG. 6 shows a frequency content of an example signal acquired by one the sensors. FIG. 7 illustrates the positioning of sensors and acoustic sources.

Choice of the Localization Method

Figure 8:
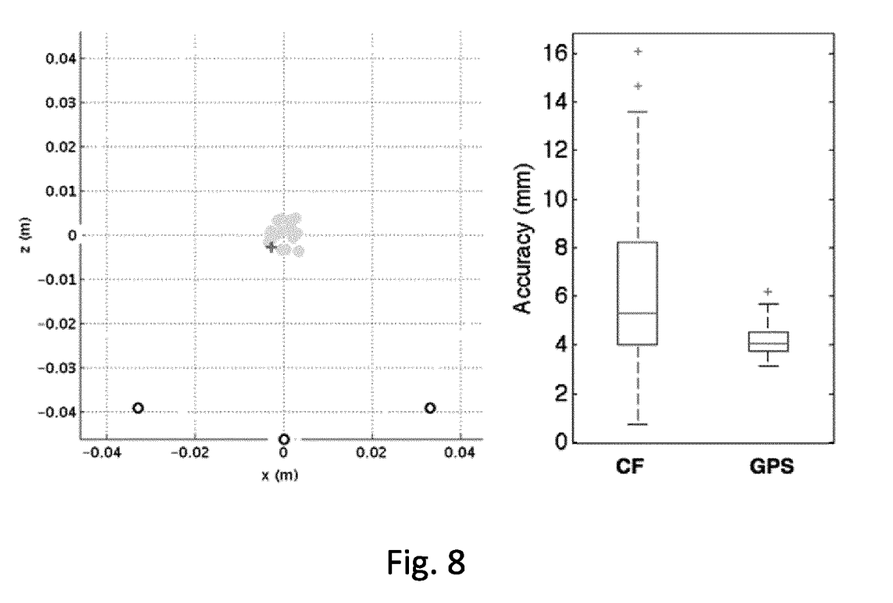
FIG. 8 is a representation of performances in terms of mean distance between calculated point and acoustic sources of two calculation methods implemented for calculating the localization of the region of interest based on the delays, illustrating, on the left, a localization example for 20 acoustic sources with a calculation method implementing hyperbolic solutions, and, on the right, an expected accuracy from simulations performed for 1 to 40 acoustic sources by a method implementing minimization of a cost function (CF) and the method implementing hyperbolic solutions of hyperbolic solutions (GPS)

Simulations are run for 1-40 synthetic cavitation sources distributed randomly in a 5 mm-sided cube. The location calculation from the measured delays is processed in parallel for the same bubble distributions for the two calculation methods. FIG. 8 presents the localization performances of both calculation methods in terms of the mean distance between the calculated point and the sources. The mean accuracies are 5 mm and 4 mm for the calculation methods based on minimization of the cost function and on hyperbolic solutions, respectively. However, there is a higher variability of the accuracy with the calculation method based on the cost function. Moreover, the calculation time is around 50 ms for the cost function versus 0.5 ms for the hyperbolic solutions (non optimized, running on Matlab with a commercial laptop—Intel i5 2.4 GHz (two cores), 4 GB RAM). This difference is mainly explained by the fact that hyperbolic solutions is an explicit method. This makes the hyperbolic solutions method a better choice regarding both the reliability and the calculation time.

Experimental Setup

Figure 9:
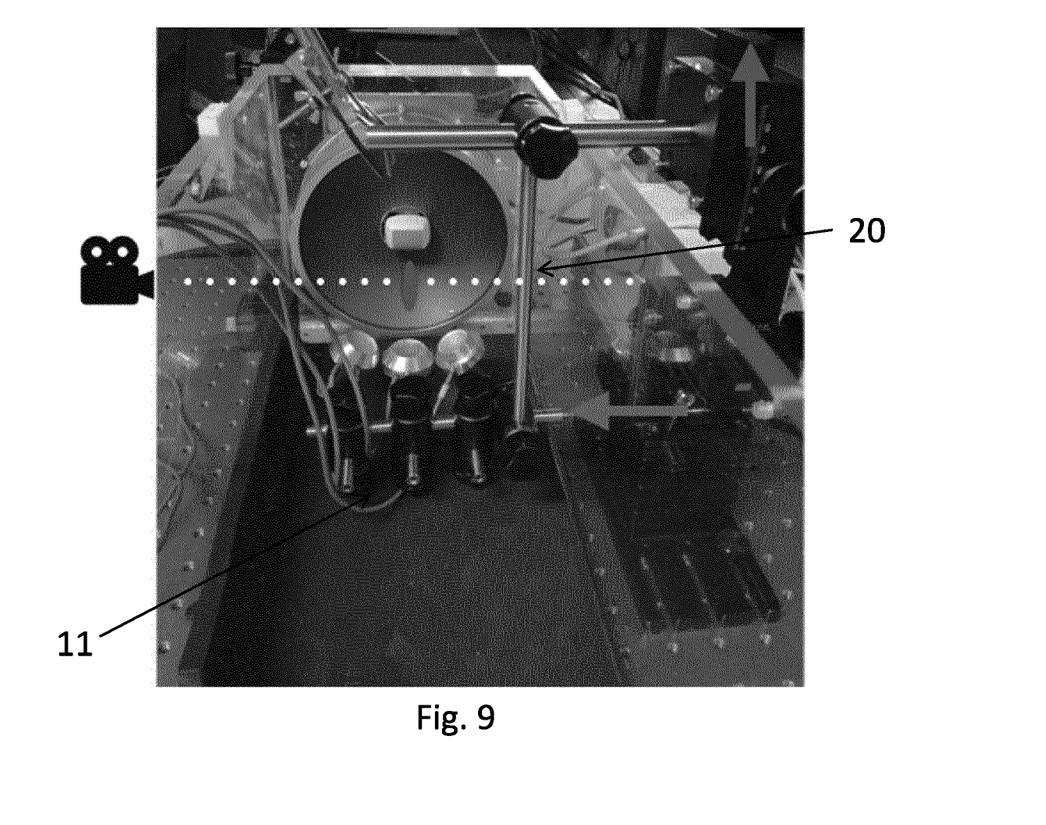
FIG. 9 is a representation of an experimental setup for performing the simulation, a high speed camera being arranged to have an observation plan orthogonal to a source localization plan, sensor network displacements being represented by two arrows.

As shown on FIG. 9, to validate experimentally the method, an antenna of three sensors, especially hydrophones 11, is attached on a movable arm 20 and placed in a degassed-water tank (2 mg/L Oxygen) with an included focused transducer. The transducer generates a single pulse at a peak pressure in the 15 MPa order for 50 cycles at 1 MHz that creates a well defined cavitation cloud in a reproducible manner. A high-speed camera is oriented to image the plane that is orthogonal to the localization plane and synchronized with the ultrasound pulse. The resulting images are used to verify the correct formation of the cavitation cloud for each pulse. The cavitation signals are recorded through a digital oscilloscope at 100 MHz sampling frequency. The acquisitions are performed while moving the antenna to several locations under the cavitation cloud. After filtering around the 1.5 ultra-harmonic and extraction of the signal envelope, the cavitation signals are processed by the localization algorithm to evaluate if the relative displacement of the acoustic source is correctly detected. The experimentation is repeated both in water and in chicken breast. In this last case, the emergence of the 1.5 ultra-harmonic stands for the presence of cavitation.

Configuration Optimization

Figure 10:
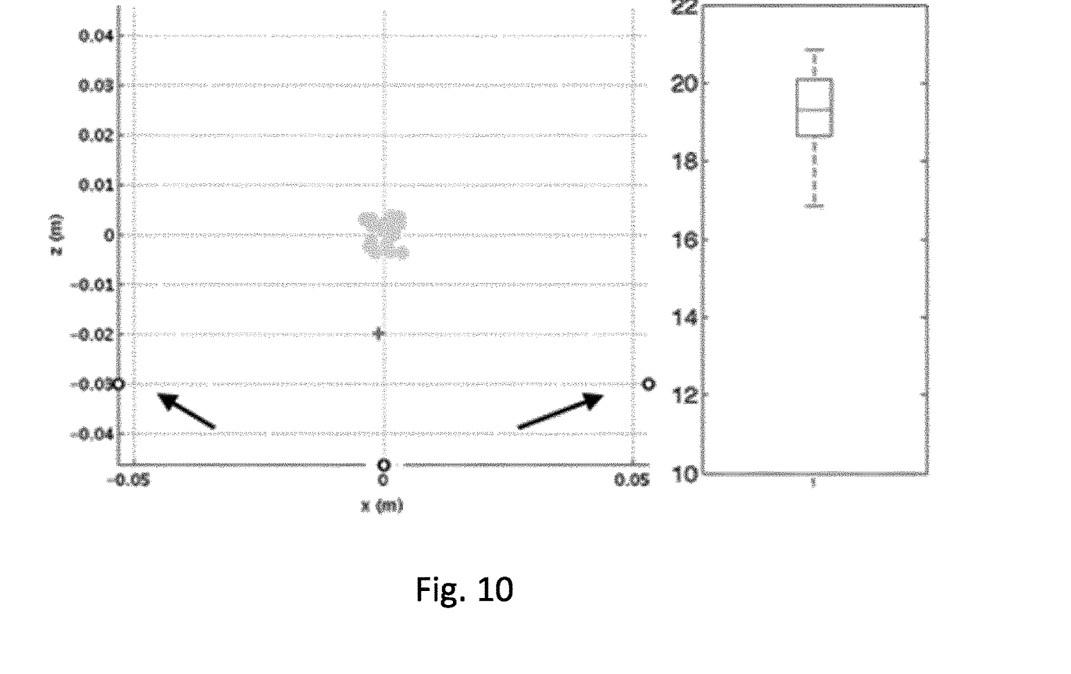
FIG. 10 is a representation of an expected accuracy in simulated localization while increasing an angle between the sensors, illustrating, on the left, a configuration with 20 sources and a change in the sensor positions with respect to the experimental setup represented by arrows, and, on the right, a statistic repartition of the localization accuracy.
Figure 11:
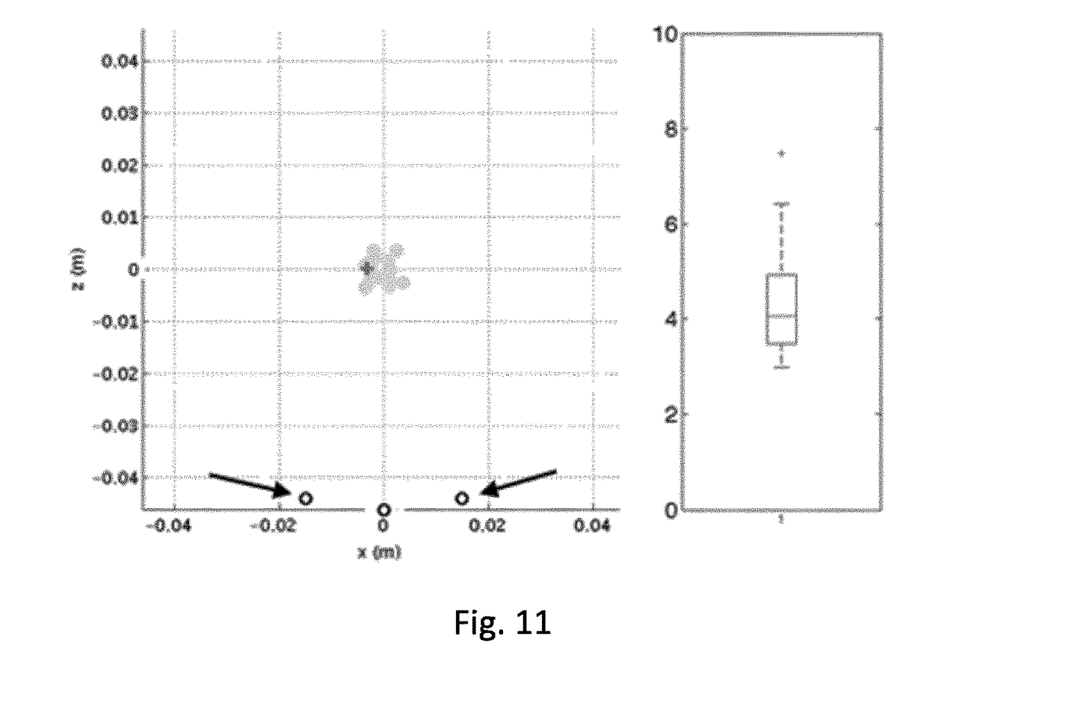
FIG. 11 is a representation of an expected accuracy in simulated localization while decreasing an angle between the sensors, illustrating, on the left, a configuration with 20 sources and a change in the sensor positions with respect to the experimental setup represented by arrows, and, on the right, a statistic repartition of the localization accuracy.

Using the hyperbolic solutions method, the effect of the position of the transducers is briefly evaluated numerically. FIG. 10 and FIG. 11 present the expected accuracy is increasing or decreasing the angle between the receptors, respectively. Surprisingly, while the accuracy stays acceptable when reducing the separation angle, it gets deteriorated when increasing the angle.

Surprisingly, a wider separation angle is not necessarily better. This could be explained by the fact that, because of the large number of interferences between the sources in the focal zone, the emitted signal is not identical for all directions. Thus, two hydrophones that are spatially close to each other will acquire signals with an information content that is also close. The intercorrelation can thus be precise and result in the correct delay estimation. Contrarily, two sensors that are distant from each other may receive signal that are poorly correlated. This can induce the inaccuracy of the inter-correlation maximum determination and thus result in an inaccurate evaluation of the delay.

Results

Cavitation Observations

Figure 12:
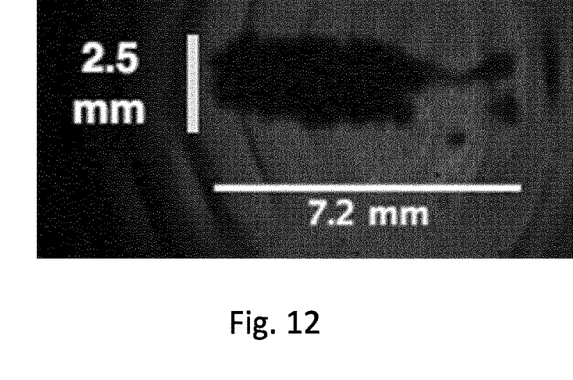
FIG. 12 is an image of a generated cavitation cloud acquired by the high speed camera of the experimental setup.

As shown on FIG. 12, the cavitation events are observed in the plan that is orthogonal to the localization plane. From the acquired images, the size of the cavitation cloud was measured to be 2.5 mm in the localization plane and 7.2 mm in the orthogonal direction.

Simulations

Figure 13:
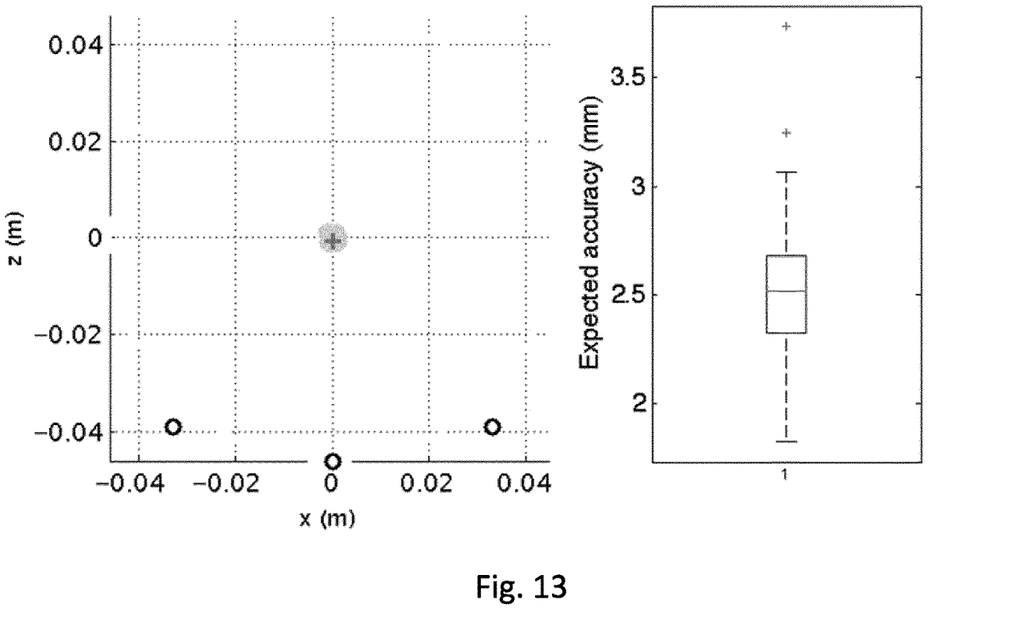
FIG. 13 is a representation of expected results from simulations mimicking the experimental conditions.

According to the measured size of the cavitation cloud, the localization process is simulated for a source spreading of 2.5 mm in both direction of the localization plan and 7.2 mm in the orthogonal direction. The FIG. 13 presents the expected accuracy from the simulation mimicking the experimental conditions. This expected accuracy would be between 2 mm and 3 mm, which corresponds to the spatial spreading of the sources in the localization plane.

Figure 14:
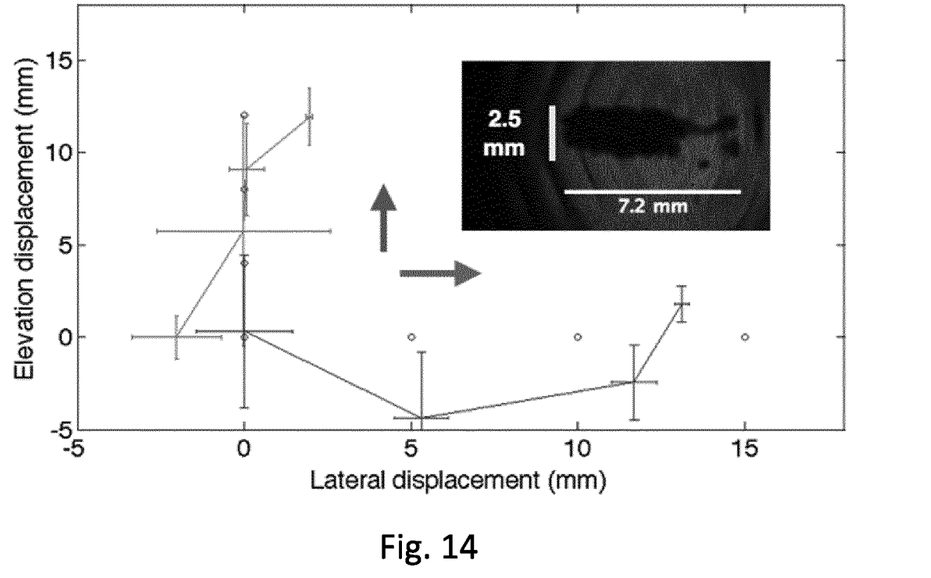
FIG. 14 is a representation of a tracking of the relative displacement of the acoustic source in water.
Figure 15:
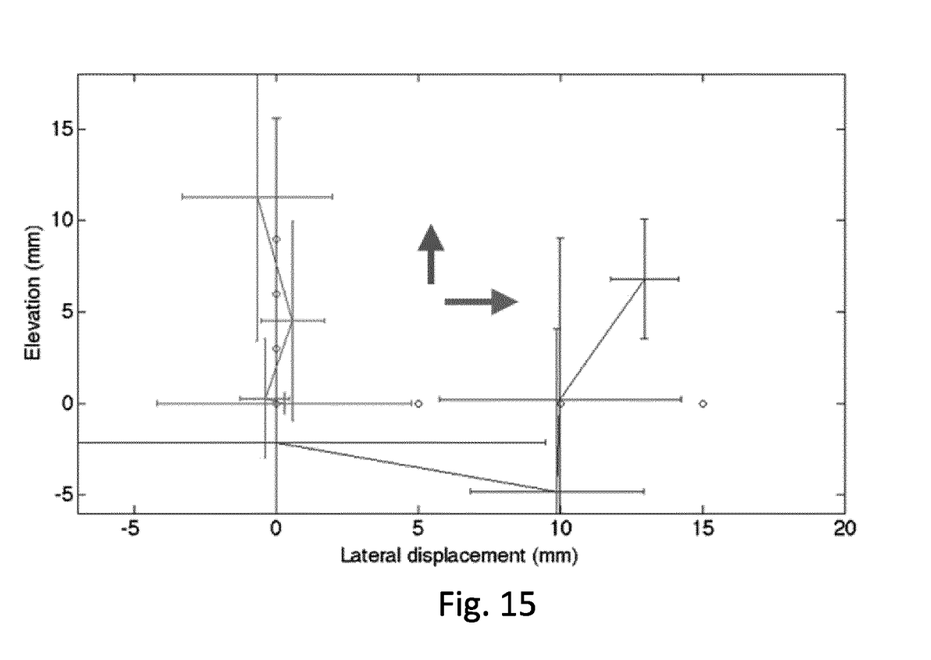
FIG. 15 is a representation of a tracking of the relative displacement of the acoustic source in chicken breast.
Figure 16:
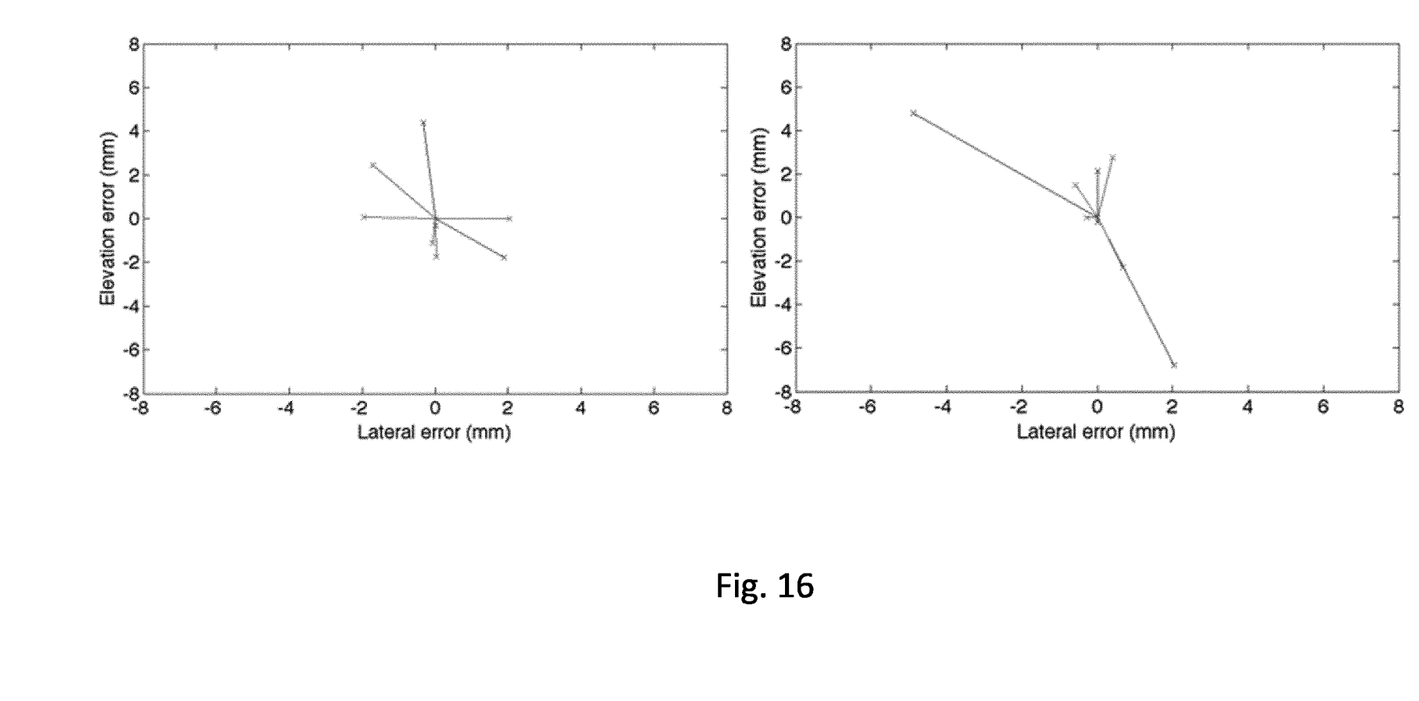
FIG. 16 is a representation of mean localization error in water (left) and in chicken breast (right).

Experimental Validation p FIG. 14 and FIG. 15 present the localization of the cavitation cloud (in water and chicken breast, respectively), while displacing the source relatively to the antenna. The cavitation cloud is displayed on scale on the water experiment results. Even if relatively important errors appear on the localization in chicken breast, it is still possible to track the movement of the cavitation cloud relatively to the receptor antenna. This proves that the method is able to correctly identify the position of the cavitation cloud relatively to the receptor network.

The invention claimed is:

1. Method for localizing a region of interest in a medium in which cavitation occurs, comprising:
   producing cavitation in the region of interest, the cavitation generating an acoustic signal,
   at each of at least three separate positions, detecting a cavitation signal representative of the acoustic signal of the cavitation,
   for at least two pairs of cavitation signals, determining a delay between the cavitation signals of each pair of cavitation signals,
   calculating a localization of the region of interest based on the delays and the positions,
   wherein the step of determining the delay comprises, for each pair of cavitation signals:
   incrementally shifting one of the cavitation signals with respect to the other according to a time lapse,
   at each time lapse, comparing the cavitation signals,
   identifying a maximum inter-correlation time lapse as the time lapse at which the cavitation signals overlap at a maximum,
   calculating the delay as a sum of the time lapses up to the maximum inter-correlation time lapse,
   wherein the step of calculating a localization of the region of interest comprises:
   converting the delays to distances, for a number of points of a space including the region of interest, each point having determined coordinates (x, y), minimizing a cost-function $$C(x, y) = \sum_{i=2}^{n} [(r_1(x, y) - r_i(x, y)) - \varepsilon_i]^2 \quad (1)$$

with n integer greater than or equal to 3 is the number of positions, $$r_i = \left\| \begin{matrix} x_i - x \\ y_i - y \end{matrix} \right\|,$$

distance between position i and acoustic source, $\varepsilon_i$, distance between positions i and 1 determined from the conversion of the delays to distances.

2. Method according to claim 1, wherein the step of detecting the cavitation signal comprises providing at least three hydrophones at respective separate positions and directing the hydrophones towards an area including the region of interest.

3. Method according to claim 1, wherein the acoustic signal of the cavitation has at least one specific frequency, and wherein said method comprises, before the step of determining the delay, a step consisting in filtering each cavitation signal with a bandwidth around the at least one specific frequency, the bandwidth being preferably between 25% and 75% of the at least one specific frequency.

4. The method of claim 3, wherein the bandwidth is between 30% and 60% of the at least one specific frequency.

5. Method according to claim 1, wherein the step of producing cavitation comprises emitting at least first and second ultrasound beams along first and second directions intersecting at a focal point, the first and second ultrasound beams being adapted to generate cavitation in a focal area around the focal point.

6. Method according to claim 5, wherein
the step of detecting the cavitation signal comprises providing at least three hydrophones at respective separate positions and directing the hydrophones towards an area including the region of interest, and
the step of detecting the cavitation signal comprises directing the hydrophones towards the focal area.

7. Method according to claim 5,
wherein the acoustic signal of the cavitation has at least one specific frequency, and wherein said method comprises, before the step of determining the delay, a step consisting in filtering each cavitation signal with a bandwidth around the specific frequency, the bandwidth being between 25% and 75% of the specific frequency, and
wherein the first and second ultrasound beams have an emission frequency $f_e$, and wherein the at least one specific frequency of the acoustic signal of the cavitation is between $0.4 \times f_e$ and $0.6 \times f_e$.

8. Method according to claim 5,
wherein the acoustic signal of the cavitation has at least one specific frequency, and wherein said method comprises, before the step of determining the delay, a step consisting in filtering each cavitation signal with a bandwidth around the specific frequency, the bandwidth being between 25% and 75% of the specific frequency, and
wherein the first and second ultrasound beams have an emission frequency $f_e$, and wherein the at least one specific frequency of the acoustic signal of the cavitation is between $1.2 \times f_e$ and $2.2 \times f_e$.

* * * * *